US008797069B2

(12) United States Patent
Hesen et al.

(10) Patent No.: US 8,797,069 B2
(45) Date of Patent: Aug. 5, 2014

(54) HIGH SPEED RF DIVIDER

(71) Applicant: ST-Ericsson SA, Plan-les-Ouates (CH)

(72) Inventors: Leonardus Hesen, Hegelsom (NL); Paul Mateman, Millingen aan de Rijn (NL); Johannes Petrus Antonius Frambach, Nijmegen (NL)

(73) Assignee: STMicroelectronics International N.V., Plan-les-Ouates, Geneva (CH)

( * ) Notice: Subject to any disclaimer, the term of this patent is extended or adjusted under 35 U.S.C. 154(b) by 0 days.

(21) Appl. No.: 13/910,366

(22) Filed: Jun. 5, 2013

(65) Prior Publication Data

US 2013/0293272 A1  Nov. 7, 2013

Related U.S. Application Data

(62) Division of application No. 13/248,143, filed on Sep. 29, 2011, now Pat. No. 8,487,669.

(60) Provisional application No. 61/388,076, filed on Sep. 30, 2010.

(51) Int. Cl.
  *H03K 21/00* (2006.01)
(52) U.S. Cl.
  USPC .............................. 327/115; 327/117; 327/255

(58) Field of Classification Search
  USPC .................................. 327/115, 117, 254, 255
  See application file for complete search history.

(56) References Cited

U.S. PATENT DOCUMENTS

| | | | |
|---|---|---|---|
| 6,081,165 A * | 6/2000 | Goldman | 331/57 |
| 8,344,765 B2 * | 1/2013 | Qiao et al. | 327/118 |
| 8,487,669 B2 * | 7/2013 | Hesen et al. | 327/115 |

* cited by examiner

*Primary Examiner* — Hai L Nguyen
(74) *Attorney, Agent, or Firm* — Coats and Bennett, P.L.L.C.

(57) ABSTRACT

High-speed RF differential, Quadrature, divide-by-2 clock divider designs are based on inverters and clocking circuits connected in a serial ring formation. In one embodiment, only NMOS transistors are used in the inverters, and only PMOS transistors are used in the clocking circuits. This structure uses only 12 transistors. The input can be coupled directly to a VCO output, and provides minimum loading, as each VCO output is connected to only two transistors. Another embodiment comprises clocked inverter stages connected in a serial ring configuration with inverters between stages. The RF clock (or VCO signal) is used at the outer side of the inverters for speed improvement. In both circuits, positive and negative clock inputs are connected alternately at each stage of the ring.

4 Claims, 6 Drawing Sheets

HIGH SPEED RF DIVIDER

PRIORITY CLAIM

The present application is a divisional filing of U.S. patent application Ser. No. 13/248,143, titled "High Speed RF Divider", filed with the US Patent Office on Sep. 29, 2011, now U.S. Pat. No. 8,487,669, which issued on Jul. 16, 2013. The present application additionally claims priority to U.S. Patent Application Ser. No. 61/388,076, titled "High Speed RF Divider", filed with the US Patent Office on Sep. 30, 2010, the disclosure of which is incorporated herein by reference in its entirety.

TECHNICAL FIELD

The present invention relates generally to RF clock dividers, in particular to high speed RF differential, quadrature clock divider designs.

BACKGROUND

Radio Frequency (RF) clock dividers are well known and commonly used in communication systems. The clock divider is an important building block in many RF circuits, such as the phase-locked loop (PLL) circuit. In a typical PLL, the output of a voltage-controlled oscillator (VCO) is divided down by a clock divider to a frequency output by a temperature-compensated crystal oscillator (TCXO) (e.g., typically from 10 MHz to 30 MHz). The divided signal and TCXO frequencies are compared in a phase/frequency detector, and the output difference signal is filtered and used to adjust the VCO output frequency.

Another important application of a clock divider is to generate related clock signals having certain phase relationships. Most modern wireless communication systems employ modulation schemes utilizing complex values, with modulated symbols occupying both In-phase (I) and Quadrature (Q) vector space, where the I and Q axes represent a phase shift of 90 degrees. Frequency downconverting mixers and demodulators are thus commonly implemented with separate I and Q signal paths. Hence, a clock divider that not only frequency-divides a periodic signal from a source (e.g., a crystal oscillator or VCO), but also supplies the divided clock in two outputs, one phase-shifted by 90 degrees from the other, is particularly advantageous. Compared with analog resistor and capacitor (RC) quadrature generation techniques, the multi-phase frequency divider approach is easier to implement, consumes lower power, and offers smaller phase imbalance.

FIG. 1 depicts a conventional, latch-ring implementation of a balanced, quadrature-phase, divide-by-two clock divider circuit. This architecture is based on two D-latches connected in series, and clocked by alternate phases of a differential clock signals. "Cp" is a positive clock signal clocking the first D-latch. "Cn" is a balance, negative clock signal—180 degrees out of phase with Cp—clocking the second D-latch. The input of the first latch is the inverted output of the second latch. The outputs AA and CC comprise one balanced clock output having half the frequency of Cp/Cn. The outputs BB and DD comprise a second balanced clock output, also having half the frequency of Cp/Cn, and being 90 degrees out of phase with AA/CC.

Conventional RF clock divider circuits often exhibit numerous deficiencies. They have a limited maximum operating frequency, and/or high current consumption. They may lack a full swing output signal swing (rail-to-rail). Some designs are not balanced, or not fully differential. Some designs impose a high capacitive load in the driving circuit, (e.g., a VCO). In addition, some divider topologies have limited sensitivity when the input signal is small.

SUMMARY

According to embodiments of the present invention, high-speed RF differential, Quadrature, divide-by-two clock divider designs are based on inverters and clocking circuits connected in a serial ring formation. In one embodiment, only NMOS transistors are used in the inverters, and only PMOS transistors are used in the clocking circuits. This structure uses only 12 transistors. The input can be coupled directly to a VCO output, and provides minimum loading, as each VCO output is connected to only two transistors. These advantages, and excellent symmetry, make this embodiment particularly applicable as a high speed divider for direct coupling to a RF VCO. Another embodiment comprises clocked inverter stages connected in a serial ring configuration with inverters between stages. The RF clock (or VCO signal) is used at the outer side of the inverters for speed improvement. In both circuits, positive and negative clock inputs are connected alternately at each stage of the ring.

One embodiment relates to an RF quadrature clock divider. The RF-divider includes a pair of latches, each comprising a cross-coupled PMOS transistor pair operative to force complimentary voltage values at the outputs of each latch. The latches are connected between a positive voltage supply node and four central nodes. The RF-divider also includes four NAND gates connected in a serial ring formation, each stage comprising a pair of stacked NMOS transistors. The NAND gates are connected between the central nodes and a ground node, and each central node connected to a gate of one transistor in each NAND gate. Positive and negative differential RF clock inputs are each connected to a gate of one transistor in each NAND gate. The positive and negative clock inputs alternate at each successive NAND gate in the ring. The latches are operative to maintain complimentary states of the central nodes when the NAND gates are inactive. During each phase of the input clock, one NAND gate is active and operative to invert the outputs of an associated latch.

Another embodiment relates to an RF quadrature clock divider. The RF-divider includes positive and negative differential RF clock inputs and four clocked inverter stages connected in a serial ring formation. Each clocked inverter stage comprises a pair of stacked PMOS transistors connected to a pair of stacked NMOS transistors. An inverter is interposed between each clocked inverter stage. One of the PMOS transistors of each clocked inverter stage is connected to a positive voltage supply node and one of the NMOS transistors is connected to a ground node. The gates of one PMOS transistor and one NMOS transistor of each clocked inverter stage are connected together to form an inverter. The gate of one PMOS transistor and one NMOS transistor of each clocked inverter stage are each connected to a different input clock, such that the positive and negative inputs to the PMOS and NMOS transistors alternate at each successive clocked inverter circuit in the ring.

Still another embodiment relates to RF quadrature clock divider. The RF-divider includes positive and negative differential RF clock inputs, and first positive and negative differential RF clock outputs having half the frequency of the clock inputs. The RF-divider also includes second positive and negative differential RF clock outputs having half the frequency of the clock inputs and a 90-degree phase offset from the first RF clock outputs. The RF-divider further includes a plurality of transistors configured as inverters, and a plurality of transistors configured as clocking circuits, each clocking circuit associated with an inverter.

DETAILED DESCRIPTION

Figure 1:
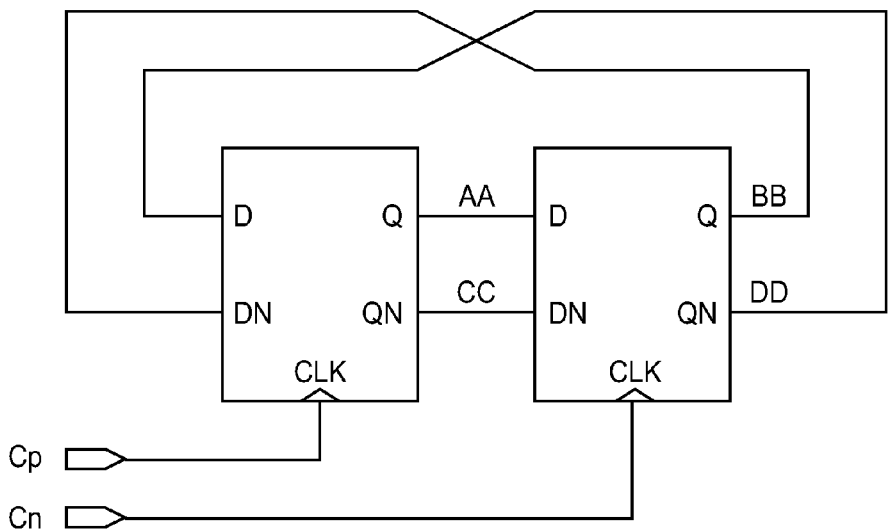
FIG. 1 is a schematic diagram of a prior art RF clock divider comprising two latches.
Figure 2A:
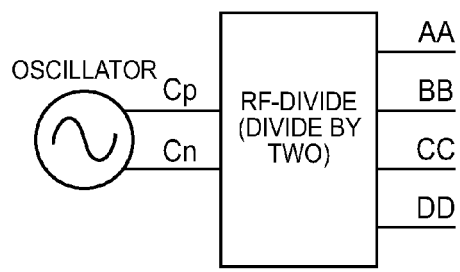
FIGS. 2A and 2B are functional block diagrams of an RF clock divider dividing the output of a VCO.

FIG. 2 depicts a typical application for RF clock dividers according to embodiments of the present invention, and demonstrates the need for a balanced, differential input with low capacitive loading, and balanced, differential, quadrature output. These circuits have particular utility in many communication system applications, where a high speed divider is needed to divide a VCO frequency to a lower frequency (e.g., in a PLL circuit). The high frequency oscillator signal is, for example, divided-by-two so that a more useable frequency is constructed that can be used for further synthesis. Additionally, multiple clock outputs having a quadrature-phase relationship are advantageous in communication system applications.

Figure 2B:
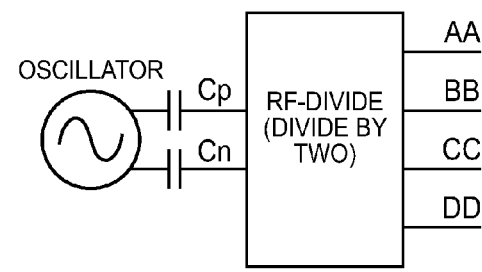

The input signal for the RF-divider is generated by a VCO. The positive input clock "Cp" and the negative input clock "Cn" are complimentary signals and the signal shape is essentially sinusoidal. Embodiments of the present invention feature a differential or balanced input, so that the RF-divider can be connected directly to the tank of the VCO. The connection between the oscillator and the divider can be done directly (FIG. 2A) or by using AC-coupling (FIG. 2B). By using AC-coupling, extra design freedom exists for making independent bias levels between the divider and the common mode level of the oscillator signal. The output nodes AA, BB, CC & DD represent the divide-by-two signals with quadrature-phase relationship. The nodes AA & CC are complemented signals, as are the nodes BB & DD.

Figure 3:
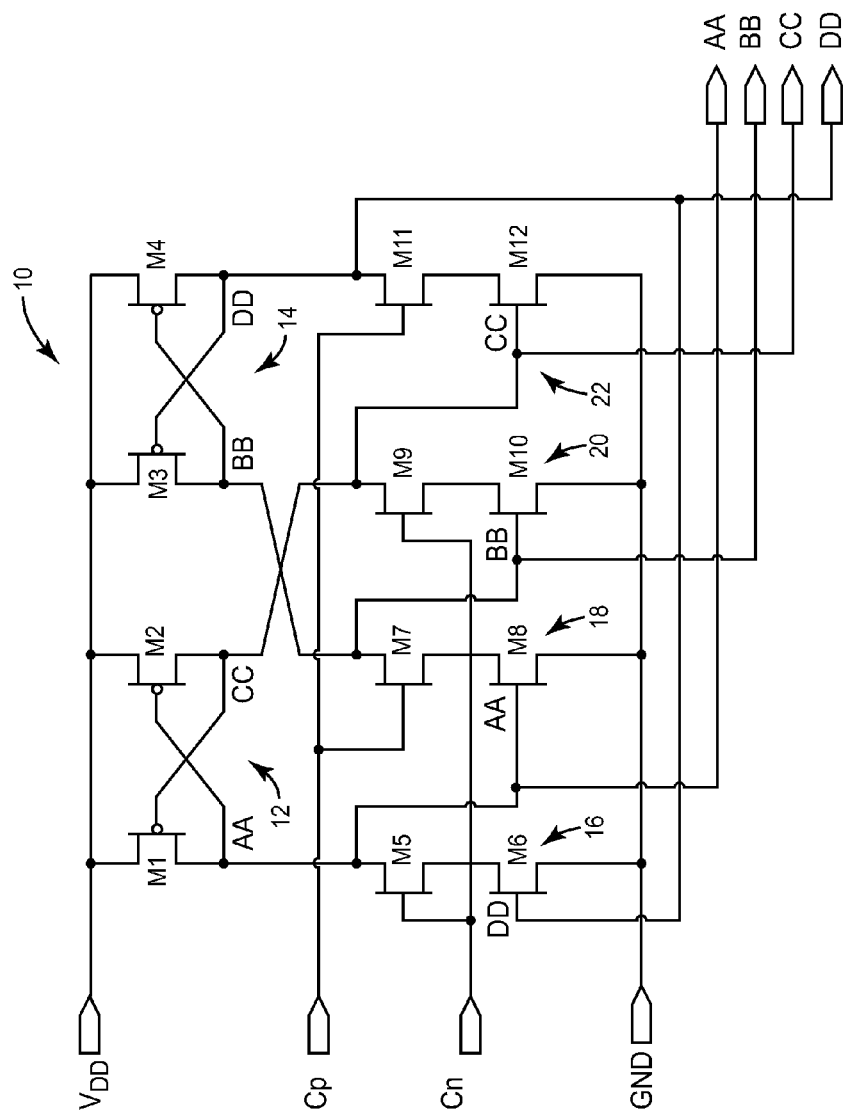
FIG. 3 is a schematic diagram of a high speed divide-by-two RF clock divider according to one embodiment of the present invention.

FIG. 3 depicts a first embodiment of a high speed, balanced, quadrature, divide-by-two RF clock divider 10. The RF-divider 10 comprises two latches 12, 14, connected to the positive voltage supply node $V_{DD}$ and four NAND gates 16, 18, 20, 22 connected to ground (the NAND gates 16, 18, 20, 22 may also be considered to be clocking circuits). The outputs of the latches 12, 14 connect to the outputs of the NAND gates 16, 18, 20, 22 at four central nodes, labeled AA, BB, CC, and DD, which are the outputs of the RF-divider 10, as explained more fully herein.

The input clock is a differential clock signal with positive signal Cp and negative signal Cn (i.e., Cn is 180 degrees out of phase with Cp). Cp and Cn are essentially sinusoidal, and may for example comprise the outputs of a VCO tank.

A first differential output clock signal is taken at the nodes AA and CC. The first output clock has half the frequency of the input clock. A second differential output clock signal is taken at the nodes BB and DD. The second output clock also has half the frequency of the input clock, and is 90 degrees out of phase with the first clock output.

Each latch 12, 14, is formed as a cross-coupled pair of PMOS transistors M1/M2 and M3/M4, respectively. The outputs AA and CC of the first latch always have opposite states. Similarly, the outputs BB and DD of the second latch 14 always have opposite states. The latches 12, 14 force the states of the central nodes AA, BB, CC, and DD when the NAND gates 16, 18, 20, 22 connected thereto are inactive.

Each NAND gate 16, 18, 20, 22 is formed as a stacked pair of NMOS transistors. That is, NAND gate 16 is formed by NMOS transistors M5 and M6; NAND gate 18 is formed by NMOS transistors M7 and M8; NAND gate 20 is formed by NMOS transistors M9 and M10; and NAND gate 22 is formed by NMOS transistors M11 and M12. As used herein, a NAND gate 16, 18, 20, 22 is "active" if both constituent NMOS transistors are "on" or in a conducting state (that is, the inputs applied to the gates of both transistors are sufficiently high voltage to exceed a switching threshold and render the transistor conductive). An active NAND gate is operative to pull its output node to (or near) ground. As used herein, a NAND gate 16, 18, 20, 22 is "inactive" if one or both constituent NMOS transistor are "off" or in a nonconducting state (that is, the input applied to the gate of at least one transistor is below its threshold level). An inactive NAND gate has no effect on the state of its output node.

The NAND gates 16, 18, 20, 22 are connected in a serial ring formation, by the gate connection of one transistor in each NAND gate being the output of the preceding NAND gate in the ring, with the output DD of the last NAND gate 22 being connected to the gate of transistor M6 of the first NAND gate 16. The positive clock Cp is connected to the gate of one transistor of every other NAND gate in the ring—i.e., transistor M7 of NAND gate 18 and transistor M11 of NAND gate 22. The negative clock Cn is connected to the gate of one transistor of every alternate other NAND gate in the ring—i.e., transistor M5 of NAND gate 16 and transistor M9 of NAND gate 20. Thus, the positive and negative input clock phases Cp, Cn alternate at each successive NAND gate in the ring.

In operation, the latches 12, 14 maintain differential, or complementary values at the output nodes when the NAND gates 16, 18, 20, 22 are inactive. During each phase of the input clock C, only one NAND gates 16, 18, 20, 22 is active, and is operative to pull its output node low. This causes the corresponding latch 12, 14 to reverse the states of its outputs. Due to the serial ring formation of the NAND gates 16, 18, 20, 22; the feedback inversion implemented by the coupling of inverter outputs to NAND gates; and the alternate phase clocking of successive NAND gate states in the ring, the resulting output pattern is half the frequency of the input clocks, with a quadrature phase difference.

Figure 4:
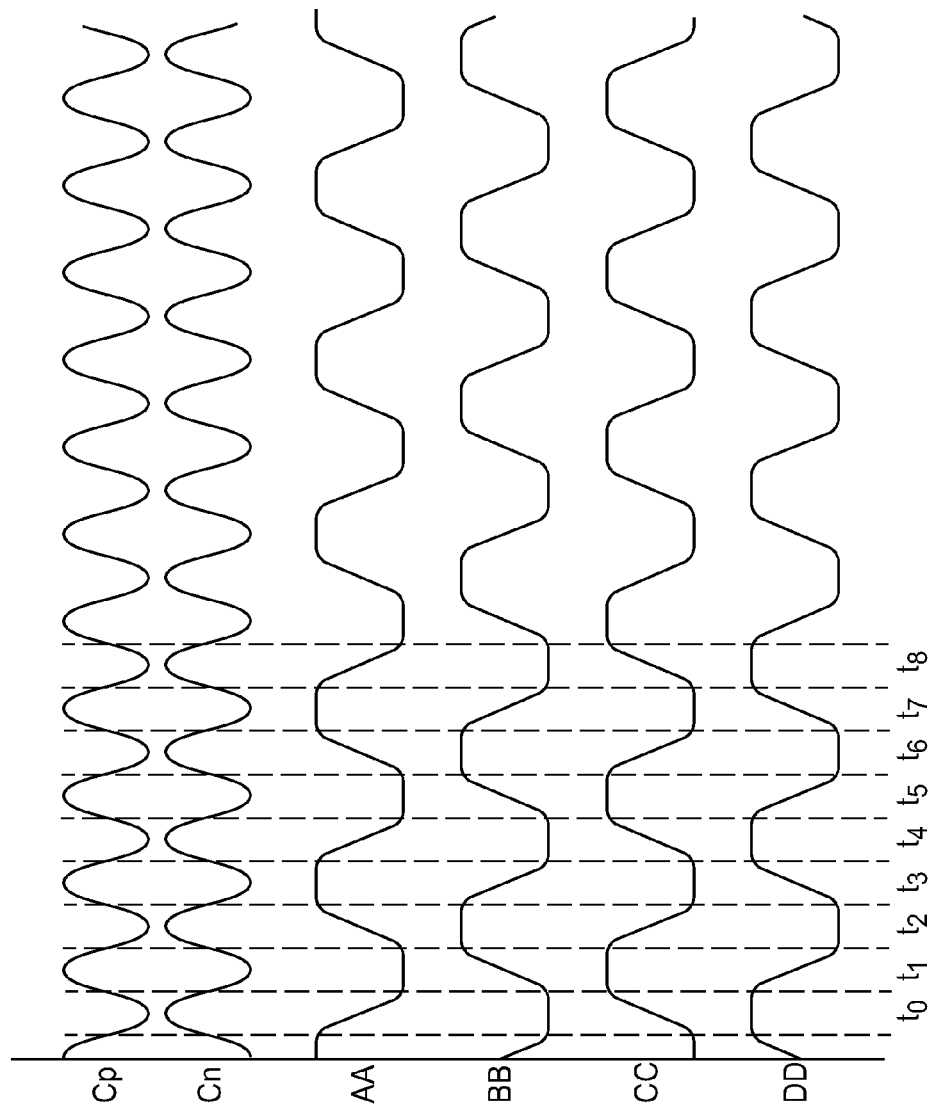
FIG. 4 is a waveform diagram of the circuit of FIG. 3.

The RF-divider 10 circuit operation is explained with reference to the state table of Table 1. For the purpose of this explanation, 1 represents a high or positive voltage value, and 0 represent a low or ground voltage level. These are the voltage levels the relevant signal achieves at the end of the input clock phase. The use of 1 and 0 is for notation only; it does not imply that the signals are square waves. Rather, the high-frequency periodic signals are generally sinusoidal, as depicted in FIG. 4. These cycles are also marked on the graph of FIG. 4.

TABLE 1

State table for RF-divider of FIG. 3

| cycle | Cp | Cn | AA | BB | CC | DD |
|---|---|---|---|---|---|---|
| $t_0$ | 0 | 1 | 0 | 0 | 1 | 1 |
| $t_1$ | 1 | 0 | 0 | 1 | 1 | 0 |
| $t_2$ | 0 | 1 | 1 | 1 | 0 | 0 |
| $t_3$ | 1 | 0 | 1 | 0 | 0 | 1 |
| $t_4$ | 0 | 1 | 0 | 0 | 1 | 1 |
| $t_5$ | 1 | 0 | 0 | 1 | 1 | 0 |
| $t_6$ | 0 | 1 | 1 | 1 | 0 | 0 |
| $t_7$ | 1 | 0 | 1 | 0 | 0 | 1 |
| $t_8$ | 0 | 1 | 0 | 0 | 1 | 1 |

At $t_0$, outputs AA and BB are 0, and the corresponding complementary outputs CC and DD are 1.

During cycle $t_1$, Cp is 1, which enables NAND gates 18 and 22. Of these, only NAND gate 22 goes active, as the CC input to M12 is also 1. The effect of NAND gate 22 being active is to pull its output node DD to 0. Latch 14 then forces output node BB to be complementary, or 1. All other NAND gates are inactive—16 and 20 because Cn=0, and 18 because AA=0. Nodes AA and CC are unchanged.

During cycle $t_2$, Cp=0 and Cn=1, which enables NAND gates 16 and 20. Of these, only NAND gate 20 goes active, as the BB input to M10 is also 1. The effect of NAND gate 20 being active is to pull its output node CC to 0. Latch 12 then forces output node AA to be complementary, or 1. All other NAND gates are inactive—18 and 22 because Cp=0, and 16 because DD=0. Nodes BB and DD are unchanged.

During cycle $t_3$, Cp=1 and Cn=0, which enables NAND gates 18 and 22. Of these, only NAND gate 18 goes active, as the AA input to M8 is also 1. The effect of NAND gate 18 being active is to pull its output node BB to 0. Latch 14 then forces output node DD to be complementary, or 1. All other NAND gates are inactive—16 and 20 because Cn=0, and 22 because CC=0. Nodes AA and CC are unchanged.

During cycle $t_4$, Cp=0 and Cn=1, which enables NAND gates 16 and 20. Of these, only NAND gate 16 goes active, as the DD input to M6 is also 1. The effect of NAND gate 16 being active is to pull its output node AA to 0. Latch 12 then forces output node CC to be complementary, or 1. All other NAND gates are inactive—18 and 22 because Cp=0, and 20 because BB=0. Nodes BB and DD are unchanged.

The states at the end of cycle $t_4$ are the same as the conditions at $t_0$. The process described above with respect to cycles $t_1$-$t_4$ will repeat over cycles $t_5$-$t_8$, and then again, and again. As one can see by looking down the column of any output, the output changes half as quickly as either input clock. One also sees that the outputs AA/CC and BB/DD are always complimentary. Consider the rows BB and AA over cycles $t_1$-$t_5$. During these cycles, output BB transitions over a full period (1100) during cycles $t_1$-$t_4$. Output AA, however, makes the same rising edge to rising edge transition over a full period (1100) during cycles $t_2$-$t_5$. Output AA thus exhibits a ¼ period (90 degrees) offset from the timing of output BB. These relationships are also apparent in the waveform diagrams of FIG. 4.

In this manner, the RF-divider 10 of FIG. 3 implements an RF, differential, quadrature, divide-by-two clock divider. The RF-divider 10 achieves this with only four PMOS transistors and eight NMOS transistors. Input clock components Cp and Cn each have a fan-out of only two NMOS transistors; hence, the RF-divider 10 does not impose significant capacitive loading on the clock generator circuit (e.g., VCO). Because the input clock signals are differential, they may be connected directly to differential circuits in the VCO tank. Because of the minimal number of transistors and simple topology, the RF-divider 10 can operate at very high speeds, occupies a minimal silicon footprint, and consumes minimal power.

Figure 5:
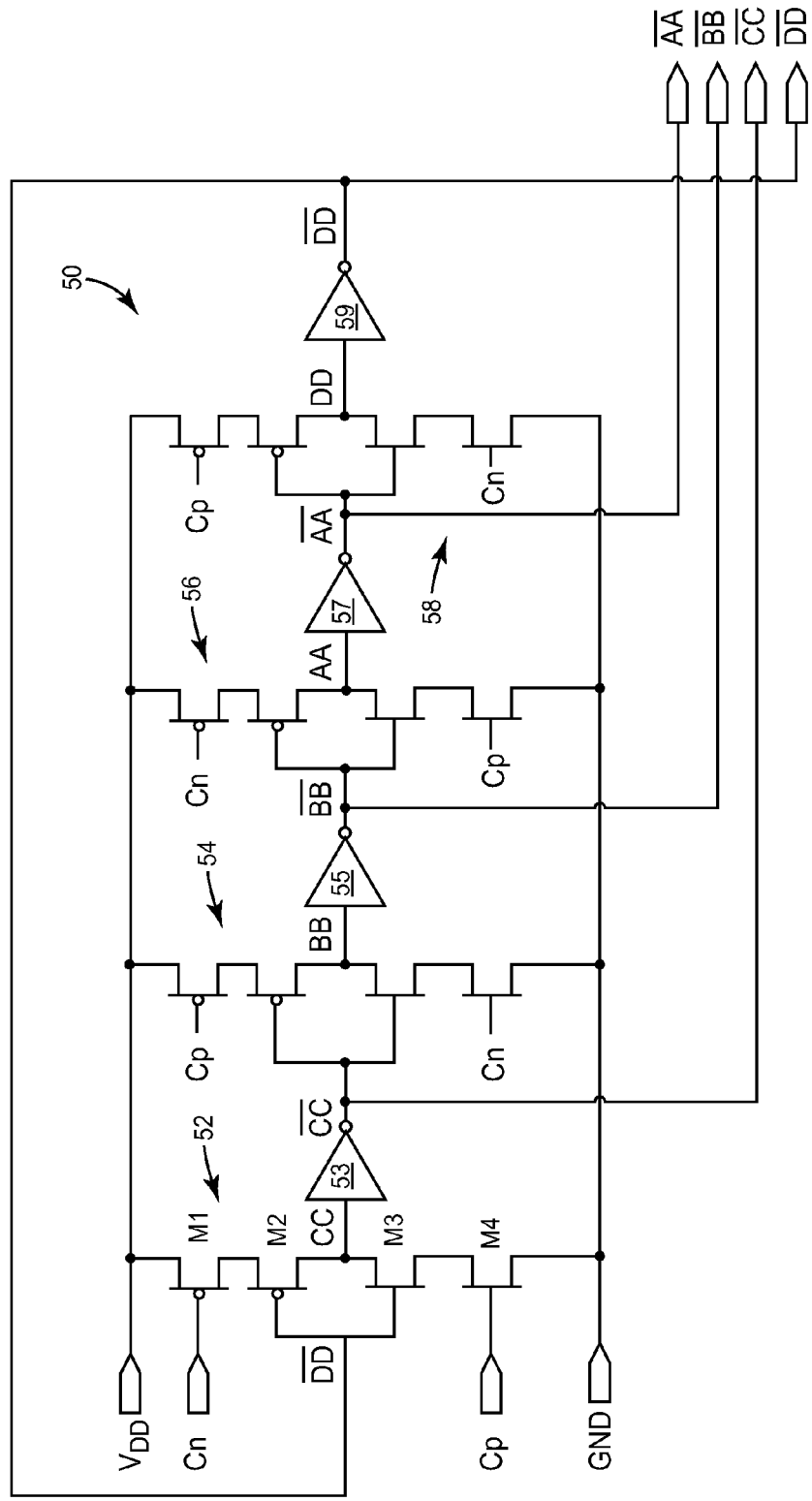
FIG. 5 is a schematic diagram of a high speed divide-by-two RF clock divider comprising inverters, according to another embodiment of the present invention.

FIG. 5 depicts a second embodiment of a high speed, balanced, quadrature, divide-by-two RF clock divider 50. The RF-divider 50 comprises four stages of serially-connected clocked inverter circuits 52, 54, 56, 58, connected between the positive voltage supply node $V_{DD}$ and ground, in a ring formation. Inverters 53, 55, 57, 59 are interposed between the clocked inverter circuits 52, 54, 56, 58. The inverters 53, 55, 57, 59 increase the speed of the RF-divider 50 by limiting the loading of each clocked inverter circuit 52, 54, 56, 58, and providing drive strength to the successive clocked inverter circuit 52, 54, 56, 58 (as well as the outputs). The input of each clocked inverter stage is thus the compliment of the output of the prior stage in the ring.

The input clock is a differential clock signal with positive signal Cp and negative signal Cn (i.e., Cn is 180 degrees out of phase with Cp). Cp and Cn are essentially sinusoidal, and may for example comprise the outputs of a VCO tank. Both input clock signals Cp and Cn are connected to each clocked inverter stage 52, 54, 56, 58, with the connections to PMOS and NMOS clock transistors switched over at each stage, as described more fully below.

The output clock signals are taken in parallel at the outputs of the inverters 53, 55, 57, 59 following each clocked inverter stage 52, 54, 56, 58. A first differential output clock signal comprises the outputs AA and CC. The first output clock has half the frequency of the input clock. A second differential output clock signal comprises the outputs BB and DD. The second output clock also has half the frequency of the input clock, and is 90 degrees out of phase with the first clock output.

The clocked inverter stages 52, 54, 56, 58 are described with reference to clocked inverter stage 52. Clocked inverter 52 comprises four stacked transistors—two PMOS transistors M1 and M2 and two NMOS transistors M3 and M4. The inner transistors M2 and M3 form an inverter, with their gates connected together and connected to a data input (the inverted output of the previous state). The outer transistors M1 and M4 form a clocking circuit; with negative input clock signal Cn connected to the gate of the PMOS transistor M1, and positive input clock signal Cp connected to the gate of the NMOS transistor M4. During one phase of the input clock, when Cp=1 and Cn=0, transistors M1 and M4 are enabled, and the output of the clocked inverter stage 52 is the compliment of the signal applied to its input. During the other phase of the input clock, when Cp=0 and Cn=1, transistors M1 and M4 are disabled, and the output of the clocked inverter stage 52 is at a high impedance (also known as tri-stated). In this case, the clocked inverter stage 52, together with the input capacitance of the next stage (or of the inverter inserted between stages 52 and 54 as a buffer) forms a sample & hold function, which retains the prior state at the output. This structure is also known in the art as clocked CMOS, or $C^2MOS$.

Which of the clock signals (Cp or Cn) connects to the PMOS or NMOS clocking transistor alternates at each stage in the ring. Accordingly, every other stage in the ring is alternately enabled.

Figure 7:
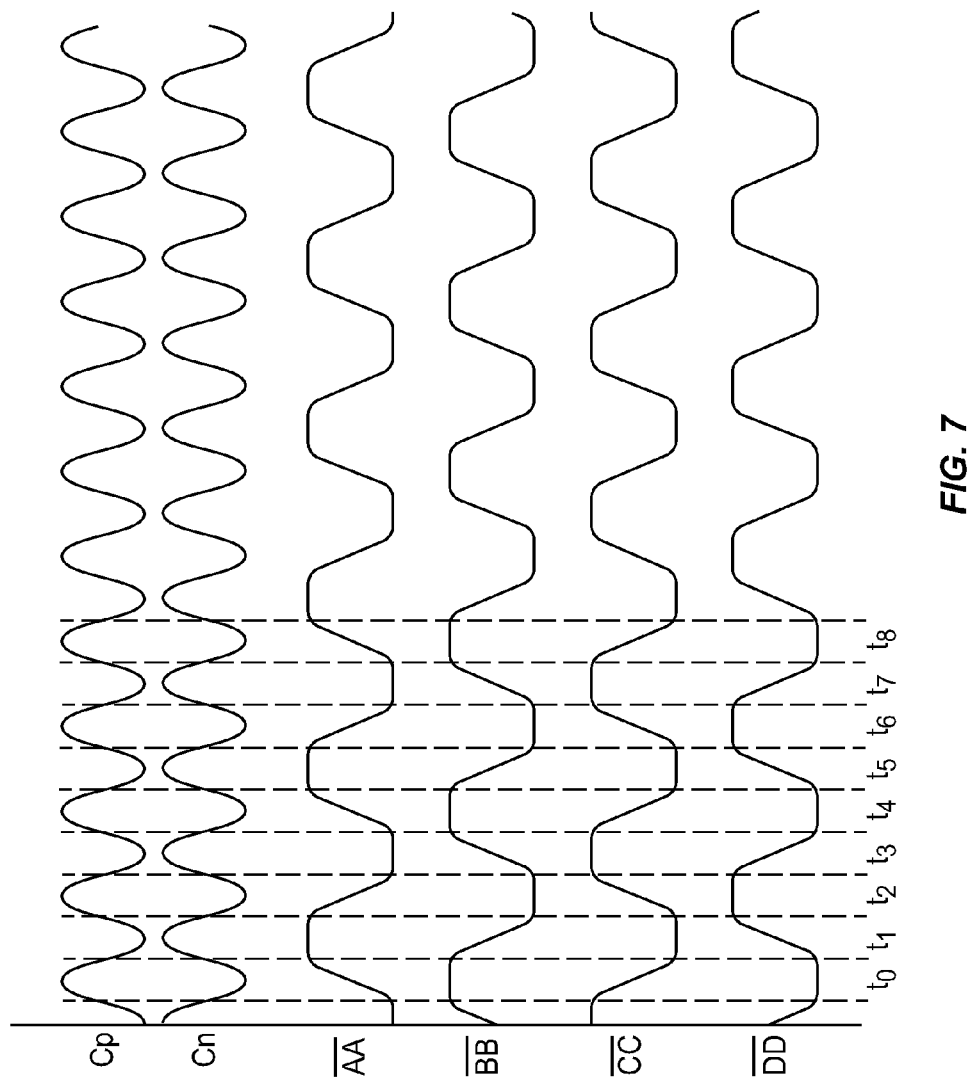
FIG. 7 is a waveform diagram of the circuits of FIGS. 5 and 6.

The RF-divider 50 circuit operation is explained with reference to the state table of Table 2. For the purpose of this explanation, 1 represents a high or positive voltage value, and 0 represent a low or ground voltage level. These are the voltage levels the relevant signal achieves (or approaches) at the end of the input clock phase. The use of 1 and 0 is for notation only; it does not imply that the signals are square waves, or that they necessarily reach the full voltage values of the power supply nodes. Those of skill in the art will appreciate that high-frequency "clock" signals, such as RF signals, are generally sinusoidal rather than square. Further, the signal excursions may not reach the power supply values ($V_{DD}$ and GND). Accordingly, a 1 herein implies a voltage excursion in the positive direction sufficiently high to exceed a threshold value and operative to cause, e.g., an NMOS transistor to become conductive. Similarly, a 0 herein implies a negative direction voltage excursion. FIG. 7 depicts the input clock signals Cp and Cn, and the RF-divider 50 outputs $\overline{AA}$, $\overline{BB}$, $\overline{CC}$ and $\overline{DD}$, taken in parallel at the outputs of inverters 57, 55, 53, and 59, respectively.

TABLE 2

State table for RF-divider of FIG. 5

| cycle | Cp | Cn | AA | $\overline{AA}$ | BB | $\overline{BB}$ | CC | $\overline{CC}$ | DD | $\overline{DD}$ |
|---|---|---|---|---|---|---|---|---|---|---|
| $t_0$ | 1 | 0 | 0 | 1 | 0 | 1 | 1 | 0 | 1 | 0 |
| $t_1$ | 0 | 1 | 0 | 1 | 1 | 0 | 1 | 0 | 0 | 1 |
| $t_2$ | 1 | 0 | 1 | 0 | 1 | 0 | 0 | 1 | 0 | 1 |
| $t_3$ | 0 | 1 | 1 | 0 | 0 | 1 | 0 | 1 | 1 | 0 |
| $t_4$ | 1 | 0 | 0 | 1 | 0 | 1 | 1 | 0 | 1 | 0 |
| $t_5$ | 0 | 1 | 0 | 1 | 1 | 0 | 1 | 0 | 0 | 1 |
| $t_6$ | 1 | 0 | 1 | 0 | 1 | 0 | 0 | 1 | 0 | 1 |
| $t_7$ | 0 | 1 | 1 | 0 | 0 | 1 | 0 | 1 | 1 | 0 |
| $t_8$ | 0 | 1 | 0 | 1 | 0 | 1 | 1 | 0 | 1 | 0 |

At $t_0$, outputs AA and BB are 0, and the corresponding complementary outputs CC and DD are 1.

During cycle $t_1$, Cp=0 and Cn=1, which enables clocked inverter stages 54 and 58. Stage 54 inverts the input $\overline{CC}$=0, clocking BB=1 to the output. Stage 58 inverts the input $\overline{AA}$=1, clocking DD=0 to the output. Nodes AA and CC are unchanged.

During cycle $t_2$, Cp=1 and Cn=0, which enables clocked inverter stages 52 and 56. Stage 52 inverts the input $\overline{DD}$=1, clocking CC=0 to the output. Stage 56 inverts the input $\overline{BB}$=0, clocking AA=1 to the output. Nodes BB and DD are unchanged.

During cycle $t_3$, Cp=0 and Cn=1, which enables clocked inverter stages 54 and 58. Stage 54 inverts the input $\overline{CC}$=1, clocking BB=0 to the output. Stage 58 inverts the input $\overline{AA}$=0, clocking DD=1 to the output. Nodes AA and CC are unchanged.

During cycle $t_4$, Cp=1 and Cn=0, which enables clocked inverter stages 52 and 56. Stage 52 inverts the input $\overline{DD}$=0, clocking CC=1 to the output. Stage 56 inverts the input $\overline{BB}$=1, clocking AA=0 to the output. Nodes BB and DD are unchanged.

The states at the end of cycle $t_4$ are the same as the conditions at $t_0$. The process described above with respect to cycles $t_1$-$t_4$ will repeat over cycles $t_5$-$t_8$, and then again, and again. As one can see by looking down the column of any output, the output changes half as quickly as either input clock. One also sees that the outputs AA/CC and BB/DD are always complimentary. Consider the rows BB and AA over cycles $t_1$-$t_5$. During these cycles, output BB transitions over a full period (1100) during cycles $t_1$-$t_4$. Output AA, however, makes the same rising edge to rising edge transition over a full period (1100) during cycles $t_2$-$t_5$. Output AA thus exhibits a ¼ period (90 degrees) offset from the timing of output BB. These relationships are also apparent in the waveform diagrams of FIG. 7.

In this manner, the RF-divider 50 of FIG. 5 implements an RF, differential, quadrature, divide-by-two clock divider. The RF-divider 50 achieves this with only eight PMOS transistors and eight NMOS transistors, in addition to the interstitial inverters 53, 55, 57, 59. Input clock components Cp and Cn each have a fan-out of only four transistors; hence, the RF-divider 50 does not impose significant capacitive loading on the clock generator circuit (e.g., VCO). Because the input clock signals are differential, they may be connected directly to differential circuits in the VCO tank. Because of the minimal number of transistors and simple topology, the RF-divider 50 can operate at very high speeds, occupies a minimal silicon footprint, and consumes minimal power.

Figure 6:
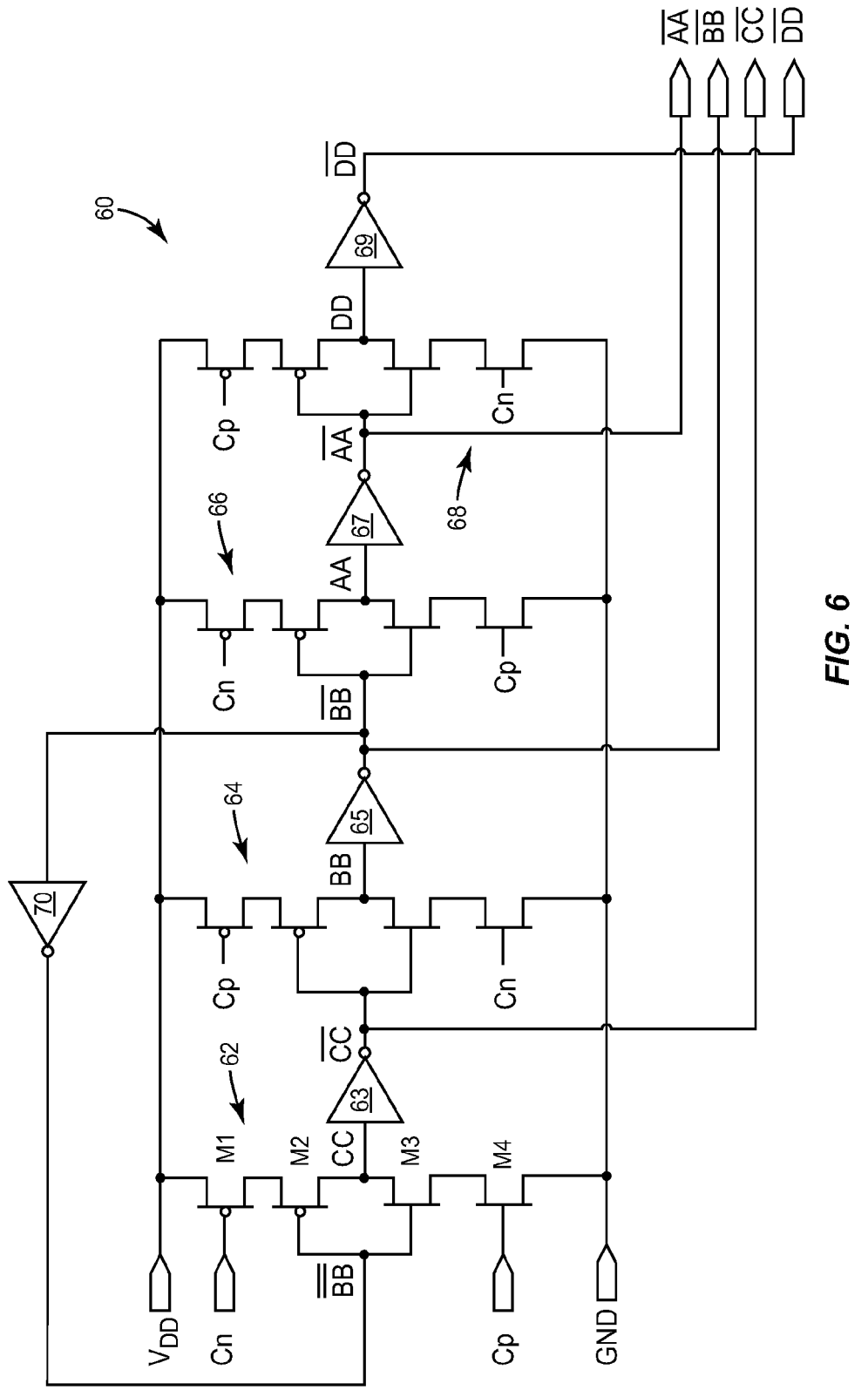
FIG. 6 is a schematic diagram of a high speed divide-by-two RF clock divider comprising an odd number of inverters, according to yet another embodiment of the present invention.

FIG. 6 depicts a third embodiment of a high speed, balanced, quadrature, divide-by-two RF clock divider 60, comprising clocked inverter circuits 62, 64, 66, 68 with interstitial inverters 63, 65, 67, 69, configured and generally operative as described with respect to RF-divider 50. In this embodiment, an additional inverter 70 is added, and the feedback for the ring is altered such that the ring includes an odd number of inverters. This guarantees proper start-up. As differential outputs, the signals BB and DD are always complimentary. Hence, $\overline{DD}$=$\overline{BB}$, and the operation of the RF-divider 60 is logically the same as described for RF-divider 50 above.

Embodiments of the present invention present numerous advantages over prior art RF clock dividers. They implement high speed, full swing CMOS divide-by-two dividers with balanced inputs and balanced quadrature outputs. VCO and clock loading are minimized with minimum transistors. The embodiments feature a fully balanced structure, and are robust against mismatch between p and n channels. The dividers feature good sensitivity for low swing VCO signals, low power, and good phase noise characteristics.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

The invention claimed is:

1. A Radio Frequency (RF) quadrature clock divider comprising:
    positive and negative differential RF clock inputs;
    four clocked inverter stages connected in a serial ring formation, each clocked inverter stage comprising a pair of stacked PMOS transistors connected to a pair of stacked NMOS transistors; and
    an inverter interposed between each clocked inverter stage;
    wherein one of the PMOS transistors of each clocked inverter stage is connected to a positive voltage supply node and one of the NMOS transistors is connected to a ground node;
    wherein the gates of one PMOS transistor and one NMOS transistor of each clocked inverter stage are connected together to form an inverter; and
    wherein the gate of one PMOS transistor and one NMOS transistor of each clocked inverter stage are each connected to a different input clock, such that the positive and negative inputs to the PMOS and NMOS transistors alternate at each successive clocked inverter circuit in the ring.

2. The RF-divider of claim 1 wherein the outputs of the clocked inverter circuits comprise first and second differential clock outputs, each having half the frequency of the clock input, and wherein the second clock output is phase shifted from the first clock output by 90 degrees.

3. A Radio Frequency (RF) quadrature clock divider comprising:
    positive and negative differential RF clock inputs;

first positive and negative differential RF clock outputs having half the frequency of the clock inputs;

second positive and negative differential RF clock outputs having half the frequency of the clock inputs and a 90-degree phase offset from the first RF clock outputs;

a first plurality of transistors configured as first inverters, wherein each of the first inverters comprises a PMOS transistor serially connected to an NMOS transistor;

a second plurality of transistors configured as clocking circuits, each clocking circuit associated with a first inverter, wherein each clocking circuit comprises a PMOS transistor interposed between an inverter and a positive voltage supply node and an NMOS transistor interposed between the inverter and a ground node;

wherein each associated first inverter and clocking circuit comprises a stage, and a plurality of such stages are connected in a serial ring formation; and a second inverter interposed between each stage;

wherein the positive clock input is connected to one transistor in each clocking circuit and the negative clock input is connected to one transistor in each clocking circuit, such that the positive and negative clock inputs alternate at each successive clocking circuit in the ring.

4. The RF-divider of claim 3 further comprising a feedback path for the ring and wherein the ring includes an odd number of second inverters.

* * * * *